United States Patent [19]

Bowen

[11] 4,385,634
[45] May 31, 1983

[54] RADIATION-INDUCED THERMOACOUSTIC IMAGING

[75] Inventor: Theodore Bowen, Tucson, Ariz.

[73] Assignee: University of Arizona Foundation, Tucson, Ariz.

[21] Appl. No.: 257,166

[22] Filed: Apr. 24, 1981

[51] Int. Cl.³ .............................................. G01K 1/00
[52] U.S. Cl. ...................................... 128/653; 73/643; 128/659; 128/660; 128/736
[58] Field of Search ...................... 73/355 R, 363, 368, 73/601, 602, 643; 128/653, 659, 660, 661, 664, 736

[56] References Cited

U.S. PATENT DOCUMENTS

| | | | |
|---|---|---|---|
| 3,771,355 | 11/1973 | Sachs | 73/597 |
| 4,246,784 | 1/1981 | Bowen | 128/339 A |

FOREIGN PATENT DOCUMENTS 2709725  9/1978  Fed. Rep. of Germany ........ 73/601

OTHER PUBLICATIONS

Bowen, "Radiation-Induced Thermoacoustic Soft Tissue Imaging", 1981 Ultrasonics Symposium, Jul. 1981.
Bowen et al., "Some Experimental Results on the Thermoacoustic Imaging of Tissue Equivalent Phantom Materials", 1981 Ultrasonics Symposium, Jul. 1981.
Rosencwaig et al., "High-Resolution Photoacoustic Thermowave Microscopy", Applied Physics Letters, vol. 36, No. 9, May 1, 1980, pp. 525-527.
Sachs, T. D. et al., "TAST: A Non-Invasive Tissue Analytic System", Proceedings of Seminar on Ultrasonic Tissue Characterization Held at NBS, Gaithersburg, Md., (May 28-30, 1975), pp. 153-163.
Thompson, J. E. et al., "Tumor Detection Using Microwave Enhanced Thermography and Computer Aided Analysis, 1979 IEEE MTT-S International Microwave Symposium, pp. 39-44.

Primary Examiner—Richard J. Apley
Assistant Examiner—George Yanulis
Attorney, Agent, or Firm—C. Lamont Whitham

[57] ABSTRACT

The acoustic wave generated by sudden thermal stress is used to obtain information non-invasively on the composition and structure of the stressed body. One or more acoustic transducers (1 and 1') are coupled with the surface of the body to intercept the acoustic wave and generate a corresponding electrical signal. The sudden thermal stress is induced by a pulse of radiation which deposits energy causing a rapid, but very small, rise of temperature. The radiation may be ionizing radiation, such as high energy electrons, photons (X-rays), neutrons, or other charged particles. The radiation may also be non-ionizing radiation, such as RF(2) and microwave electromagnetic radiation (3) and ultrasonic radiation (4). The electrical signal from the acoustic transducer (1) is amplified (5) and supplied to a digitizer (6), which provides a continuous stream of digital words corresponding to samples of the amplified signal. Because in most situations of practical interest the S/N ratio of a single pulse is much less than unity, it is necessary to signal-average the signals from many successive pulses. This is accomplished with a minicomputer or data processor (8) suitably interfaced (7) with the digitizer. The resulting data can then be suitably displayed as an image on a CRT display (9) or plotted or numerically printed out.

27 Claims, 24 Drawing Figures

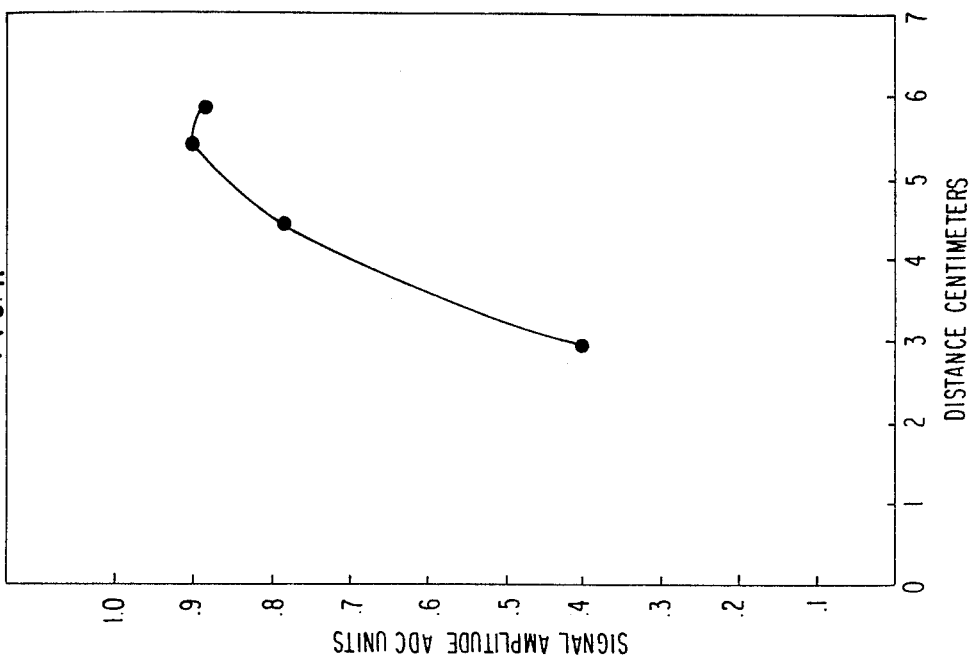
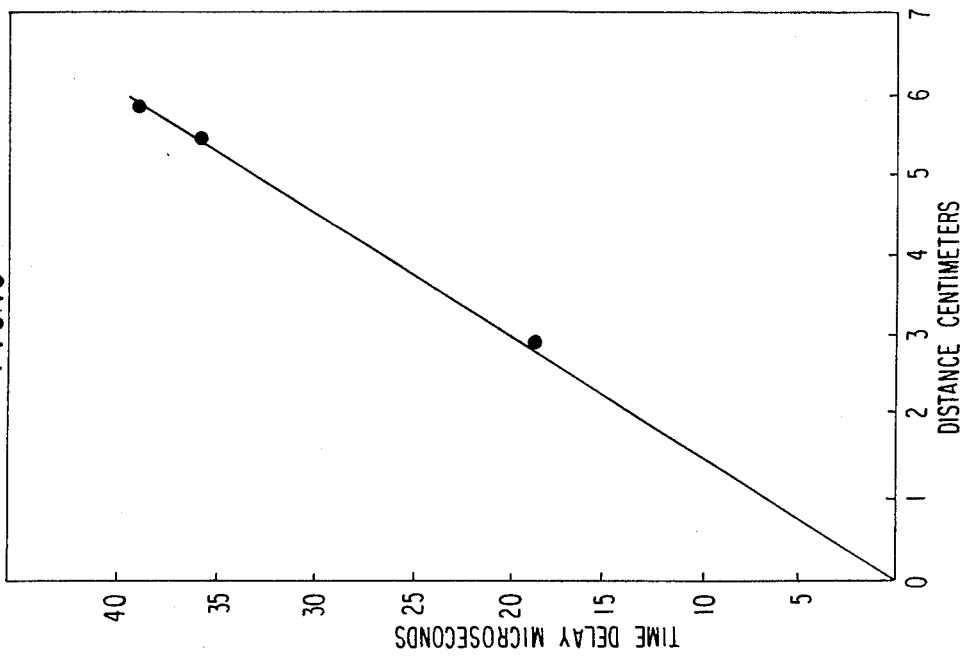

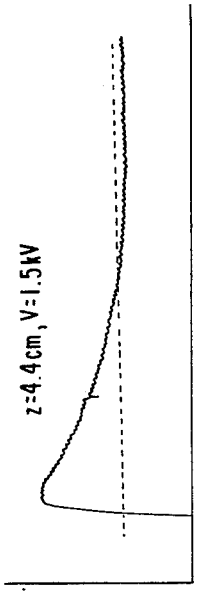
FIG.12(a) z=2.9 cm, V=1.5 kV
FIG.12(c) z=5.4 cm, V=1.0 kV
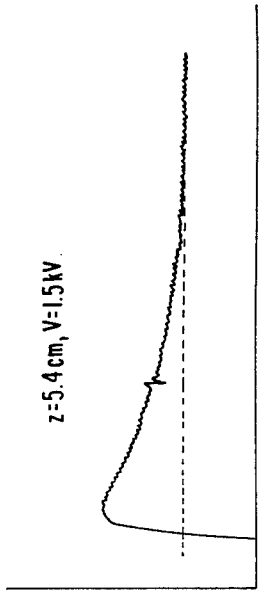
FIG.12(b) z=4.4 cm, V=1.5 kV
SIGNAL-AVERAGED WAVEFORMS CORRESPONDING TO THE DATA SHOWN IN FIGS. 9, 10 AND 11. N=10,000 PULSES EXCEPT 40,000 FOR (C).
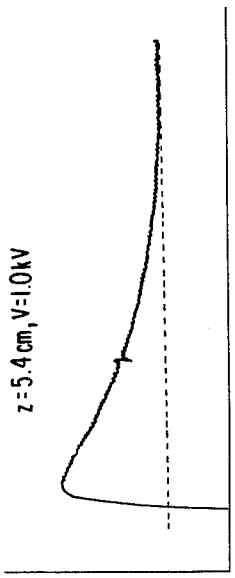
FIG.12(d) z=5.4 cm, V=1.5 kV
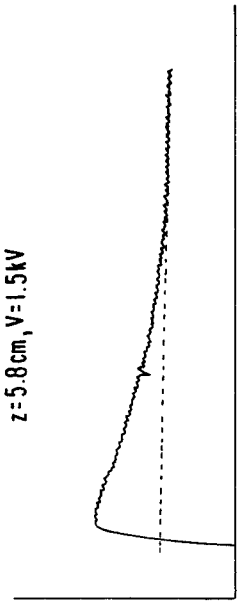
FIG.12(e) z=5.4 cm, V=2.1 kV
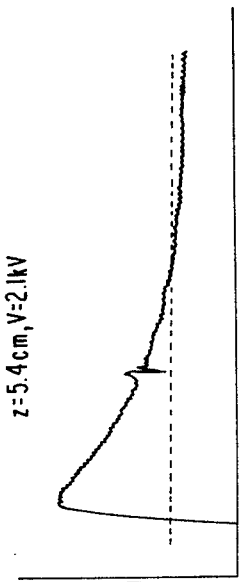
FIG.12(f) z=5.8 cm, V=1.5 kV FIG.13(a) (a) SIGNAL-AVERAGED WAVEFORM FOR THE 4-LAYER PHANTOM (N=300,000 PULSES, V=2.6kV)
FIG.13(b) (b) CORRESPONDING A-MODE ECHO SCAN (SCALE MARKS ARE 0.2cm WITH 1.0cm ACCENTED).
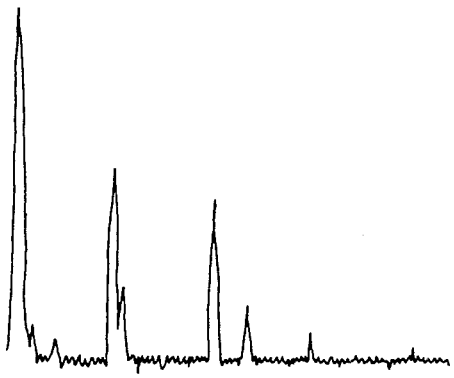

RADIATION-INDUCED THERMOACOUSTIC IMAGING

BACKGROUND OF THE INVENTION

In my prior U.S. Pat. No. 4,246,784, I have disclosed a technique for the passive non-invasive temperature measurement of the interior of a body using the acoustic thermal noise spectra of the body. According to that technique, one or more acoustic transducers are coupled to the surface of the body to intercept the acoustical noise signal from within the interior of the body along well defined paths to generate a corresponding electrical signal. The noise power spectrum of the electrical signal is analyzed by means of a power spectrum analyzer to develop an output representing the temperature-depth distribution along said paths.

The subject invention is directed to a new technique of radiation-induced thermoacoustic imaging for obtaining information non-invasively on the composition and structure of a material or body and has particular application to the imaging of soft tissue in humans and animals as well as other moderately homogeneous materials and bodies. Recent progress by the inventor and others in understanding thermoacoustic detection of charged particles shows that (a) there is a simple and direct connection between the pattern of induced thermal stress and the received pressure signals, and that (b) the signal-to-noise ratio of thermoacoustic signals relative to thermal noise can be reliably calculated. The results, when applied to thermal stress pulses induced in soft tissues by therapeutic ionizing radiation or non-ionizing (radio-frequency (RF), microwave, ultrasonic) radiation, indicate the feasibility of thermoacoustic imaging. Such images would permit (a) verification of treatment plans with respect to the positioning of therapeutic radiation dosage and (b) non-invasive identification of tissue characteristics which are not sensed by other imaging modalities.

It is known from the study of thermoelasticity by engineers, of auditory sensing of microwave pulses by biomedical researchers, and of acoustic detection of charged particles by physicists that the sudden thermal expansions due to heat pulses result in the emission of acoustic words. F. Braun, in Ann. d. Physik 65, 358 (1898), reported that temperature variations in a gas produced by passage of current through a fine resistance wire provide a source of acoustic waves. This effect was later employed in a precision sound source called the thermophone. Fairbank et al reported success with the thermophone as a sound source in liquid helium and liquid hydrogen in an article entitled "The Thermophone as a Source of Sound on Liquid Helium and Liquid Hydrogen," *J. Acoust. Sec. Am.* 19, 475 (1947).

In mechanical engineering the study of elastic deformation of bodies has evolved for more than a century, but the field of thermoelasticity, the study of elastic deformation due to thermal stresses, has mostly developed since World War II. Several textbooks are now available which discuss a wide range of problems in thermoelasticity. One class of solutions relates to the dynamic problem: where the thermal stress is applied suddenly, so the transit time for the propagation of elastic stresses (at the speed of sound) cannot be neglected. If the diffusion of heat as time progresses is properly taken into account, the problem is generally too complicated to be solved in closed form with simple analytic expressions. Fortunately, for considerations of thermoacoustic imaging, it is an excellent approximation to neglect heat diffusion. If $\Delta x$ is the size of the smallest region under consideration ($\Delta x \gtrsim 10^{-2}$ cm for soft tissue imaging because of the strong high frequency attenuation of ultrasound), c is the speed of sound ($c \approx 1.5 \times 10^5$ cm/s), and D is the thermal diffusion coefficient ($D \sim 10^{-3}$ cm$^2$/s), then heat diffusion may be neglected if $c\Delta x/D >> 1$; for soft tissue, $c\Delta x/D \sim 1.5 \times 10^6$. When heat diffusion is neglected, the solution, as will be discussed later, is fairly simple, especially if one thinks in terms of retarded potentials in analogy to those in electromagnetic theory.

Among biomedical researchers there has been considerable work in recent years which has established that the auditory sensing of microwave pulses can be explained by thermoacoustic waves induced by the sudden thermal stress due to absorption of energy from the microwave radiation field. The threshold for an auditory response in humans is most simply related to the energy deposition per unit mass (or volume) per pulse. For humans, this threshold is typically $\sim 16$ mJ/kg and for cats $\sim 10$ mJ/kg. Assuming a tissue density $\rho \approx 1$, the former figure is equivalent to 160 ergs/cm$^3$-pulse=1.6 rad/pulse. (The rad is a very convenient unit for RF or microwave heating dose, especially since we wish to make comparisons with thermoacoustic emission induced by therapeutic ionizing radiation.) Since the microwave pulse lengths are typically 1–10 $\mu$sec, the acoustic frequencies extend up to $\approx 0.1$–1 MHz. Therefore, the ear responds to only the small fraction of the emitted acoustic energy spectrum which falls in the audio frequency range. A wide-band acoustic detector optimized for maximum S/N ratio would certainly have a lower dose threshold than the auditory system.

It may be useful to briefly recite the events which led the inventor to thermoacoustic imaging. After participating in an interdisciplinary study group on ultrasonic imaging techniques in medicine, the inventor remarked in August 1975 to a group of cosmic ray scientists that the possibility of acoustic detection should be considered in connection with a proposed Deep Underwater Muon And Neutrino Detector (DUMAND) as an adjunct to the detection of the very feeble light emission by neutrino interactions in deep ocean water. A year later, the inventor and a Russian physicist independently presented calculations to the 1976 DUMAND Workshop which indicated that acoustic detection of high energy particle events might be feasible. See T. Bowen, "Sonic Particle Detection," *Proceedings of the 1976 DUMAND Summer Workshop*, University of Hawaii, Sept. 6–19, 1976, p. 523, and B. A. Dalgoshein, ibid., p. 534. The inventor's calculation began with a solution in the time domain (as distinguished from the frequency domain) for an instantaneous heat pulse given by Norwacki in his textbook entitled *Thermoelasticity*, Addison-Wesley, Reading, MA/Pergamon, Oxford (1962), at page 266. This led to a very simple way of thinking about thermoacoustic phenomena. The favorable predictions caused a number of the workshop participants, including the inventor, to form a collaboration to carry out experimental investigations in high energy proton beams. By the time the first experimental results were obtained in late 1976, a few mistakes in the first theoretical estimates were corrected, and excellent agreement was found between the thermoacoustic theory and experimental results for heating by pulses of ionizing radiation. See L. Sulak et al., "Experimental Studies of the Acoustic Signature of Proton Beams Traversing Fluid Media," *Nucl. Instrum. and Methods* 161, 203 (1979).

It was clear from the experimental and theoretical work that the acoustic signal from a single high-energy-neutrino-produced event would be very weak, and might be lost in background noise. This led the inventor at the 1977 DUMAND Workshop to work on the problem of calculating the signal-to-noise (S/N) ratio. At the suggestion of the underwater sound experts who were also participating in the workshop, the inventor studied the general theory of optimal filtering to maximize S/N and to estimate the best possible S/N. The inventor learned that the optimal S/N could be calculated for neutrino detection in a straight-forward manner. See T. Bowen, "Theoretical Prediction of the Acoustic Emission from Particle Cascades, and the Signal-to-Noise Ratio," *Proceedings of the La Jolla Workshop on Acoustic Detection of Neutrinos*, Scripps Institution of Oceanography, July 25-29, 1977, p. 37. Another participant, J. Learned, later applied this technique to detailed calculations for neutrino events of any energy and spatial orientation as reported in "Acoustic Radiation by Charged Atomic Particles on Liquids, an Analysis," *Phys. Rev.* D19, 3293 (1979).

Ironically, although the DUMAND collaboration inspired a great deal of theoretical and experimental understanding of low level thermoacoustic pressure signals, it became clear by 1979 that the energy threshold for detecting the most interesting neutrino events is too high. See T. Bowen and J. Learned, "Acoustic Detection of Ultra High Energy Neutrinos," *Proceedings of the 16th Int. Cosmic Ray Conf.*, Kyoto, Japan, August 1979, Vol. 10, p. 386, and T. Bowen, "Acoustic Detection of Ultra High Energy Neutrinos in the Deep Ocean in the Presence of High-Level Low-Frequency Noise," *Proceedings of the 1979 DUMAND Symposium and Workshop*, Khabarovsk and Lake Baikal, U.S.S.R., August 1979.

SUMMARY OF THE INVENTION

It is therefore an object of this invention to provide a new technique for obtaining information non-invasively on the composition and structures of a material or body by detecting radiation-induced thermoacoustic image features.

It is another object of the invention to provide the means for non-invasively obtaining information on soft tissue which is not obtainable by any other non-invasive technique.

The foregoing and other objects of the invention are accomplished by utilizing the acoustic wave generated by sudden thermal stress to obtain information non-invasively on the composition and structure of the stressed body. This information is denoted as an image, since it would often be displayed such as to have the appearance of a photographic image; but the means of presenting the information may take many forms, including a plot of signal vs. distance to point of origin and numerical listings of data.

The sudden thermal stress is induced by a pulse of radiation which deposits energy causing a rapid, but very small, rise of temperature (typically, $\Delta T \approx 10^{-6\circ}-10^{-5\circ}$ C.). The radiation may be ionizing radiation, such as high energy electrons, photons (X-rays), neutrons, or other charged particles. The radiation may also be non-ionizing radiation, such as R.F. and microwave electromagnetic radiation and ultrasonic radiation. Since the above radiations interact with matter via very different mechanisms, the induced patterns of thermal stresses may differ greatly, and in some cases a particular radiation may produce negligible thermal stress. The appropriate choice of radiation depends upon the nature of the body to be imaged and the type of information desired.

Any material body may be thermoacoustically imaged by some or all of the above radiations. Image features will correspond to variations of the product of heat deposition density and thermal expansion coefficient divided by specific heat. However, images will be most directly interpretable in moderately homogeneous bodies, such as the soft-tissue regions of humans and animals. By moderately homogeneous body is meant a body with inhomogeneities of sufficient magnitude to produce image features or structure, yet sufficiently homogeneous that the thermoacoustic waves can reach a surface detector without excessive attenuation due to scattering and absorption and without excessive distortion due to variations in propagation speed. Most bodies suitable for ultrasonic imaging would meet the above criteria; however, thermoacoustic imaging would in many cases give different information on the internal characteristics of the body which may either be more valuable or be complementary to the information given by ultrasonic imaging.

The thermoacoustic imaging signal is emitted from any given region when that region is impulsively heated by the external radiation. The signal is received at a later time determined by the propagation distance from the source region to a detector of acoustic pressure and/or wave motion. While a few situations may permit a radiation pulse of sufficient magnitude such that the thermoacoustic signal-to-noise (S/N) ratio is much greater than unity for a single pulse, most situations of practical interest require signal-averaging the signals from many successive pulses.

In the medical field alone, there are several potential areas of application. For example, in connection with cancer treatment by electron and X-ray beams, thermoacoustic imaging offers the possibility of verifying the beam profile, distribution of total dose, and positioning of the dose with respect to the boundaries of organs and other identifiable tissue structures. Since the signal is proportional to the ratio of thermal expansion coefficient to specific heat, $\beta/C_p$, the change of this quantity from treatment to treatment might be correlated with effects of the treatment. For example, if the water content decreased, $\beta/C_p$ would increase because water has an anomalously low value of $\beta/C_p$.

Hyperthermia as a treatment to control cancer lesions is under study in many laboratories and clinics. A serious practical problem with such treatments lies in the difficulty of uniformly heating the tumor region. Thermoacoustic imaging would permit non-invasive monitoring of the heat deposition distribution. At the same time, image features due to organ boundaries and other tissue structures would appear superimposed upon the heat deposition profile. Some changes of the image with successive treatments may be correlated with effects of the treatment in a relation unique to thermoacoustic imaging.

Pulsed RF or microwave radiation, at an average power too low to produce noticeable heating, could generate diagnostically useful thermoacoustic images of the irradiated region. Unlike the response in any other diagnostic imaging technique, the regions of differing electrical conductivity would exhibit high contrast in this method of thermoacoustic imaging. This unique response characteristic might prove to be a valuable adjunct to density and acoustic impedance responses of conventional X-ray and ultrasonic imaging in identifying tumors and other abnormal tissue states.

Short pulses of ultrasonic radiation could generate diagnostically useful thermoacoustic images of the insonified region. In this case the image would have a unique response to variations of the ultrasonic attenuation coefficient. This coefficient tends to be correlated with the collagen content of tissue, and there are claims that attenuation is abnormal in some tumor tissues. Paradoxically, although echo ultrasound signals are affected by the cumulative effects of attenuation, it is difficult to measure local variations of the attenuation with echo techniques. CAT-scanning arrangements utilizing transmitted ultrasound intensities can measure local attenuation, but are limited to examining regions of the soft tissue which can be surrounded by transducers and which have few, if any, obstructing bones or gas pockets.

BRIEF DESCRIPTION OF THE DRAWINGS

The foregoing advantages and other objects of the invention will be better understood from the following detailed description with reference to the accompanying drawings, in which:

FIG. 10 is a graph of signal time delay vs. transducer distance based on experimental results;

FIG. 11 is a graph of signal amplitude vs. transducer distance based on experimental results;

FIGS. 12a to 12f are graphs illustrating the averaged waveforms employed for the data of FIGS. 9, 10 and 11; and FIGS. 13a and 13b are graphs of the averaged waveforms and an A-mode echo scan, respectively, obtained from the four layer phantom shown in FIG. 7.

DETAILED DESCRIPTION OF THE INVENTION

Figure 1A:
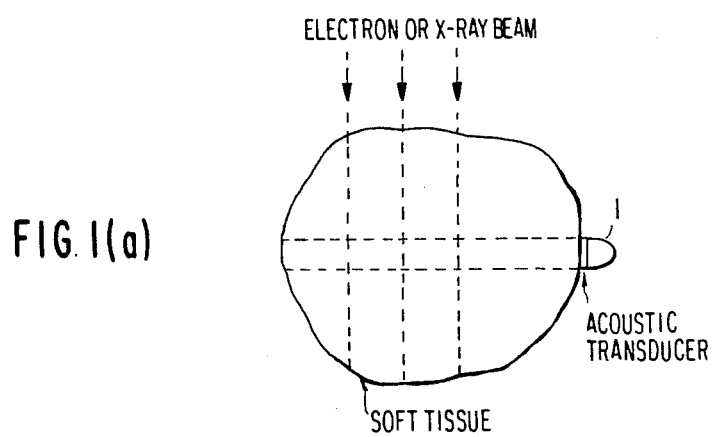
FIGS. 1a to 1d schematically illustrate various methods for inducing thermoacoustic radiation in soft tissue.
Figure 1B:
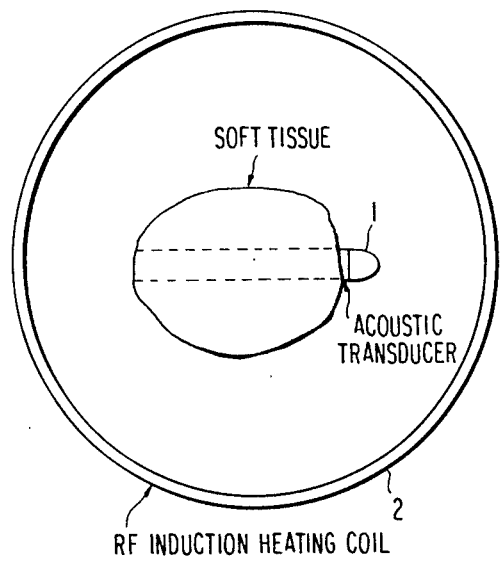
Figures 1C, 1D:
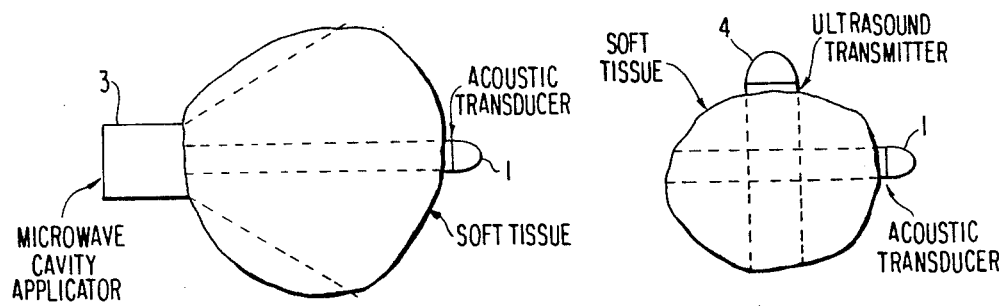

Referring now to the drawings, and more particularly to FIG. 1, there is illustrated several of the basic arrangements for inducing thermoacoustic signals. FIG. 1(a) shows ionizing radiation, such as an electron beam or an X-ray beam, directed into the soft tissue perpendicular to the receiving beam pattern of the acoustic transducer 1. FIG. 1(b) shows an induction heating coil 2 surrounding the soft tissue. FIG. 1(c) shows a microwave cavity applicator 3 positioned on the surface of the soft tissue opposite the acoustic transducer 1. FIG. 1(d) shows an ultrasound transmitter 4 positioned on the surface of the soft tissue to project a beam of ultrasound into the soft tissue perpendicular to the receiving beam pattern of the acoustic transducer 1. The acoustic transducer 1 can be a conventional piezoelectric broad-band unit designed for medical ultrasound applications.

Figure 2:
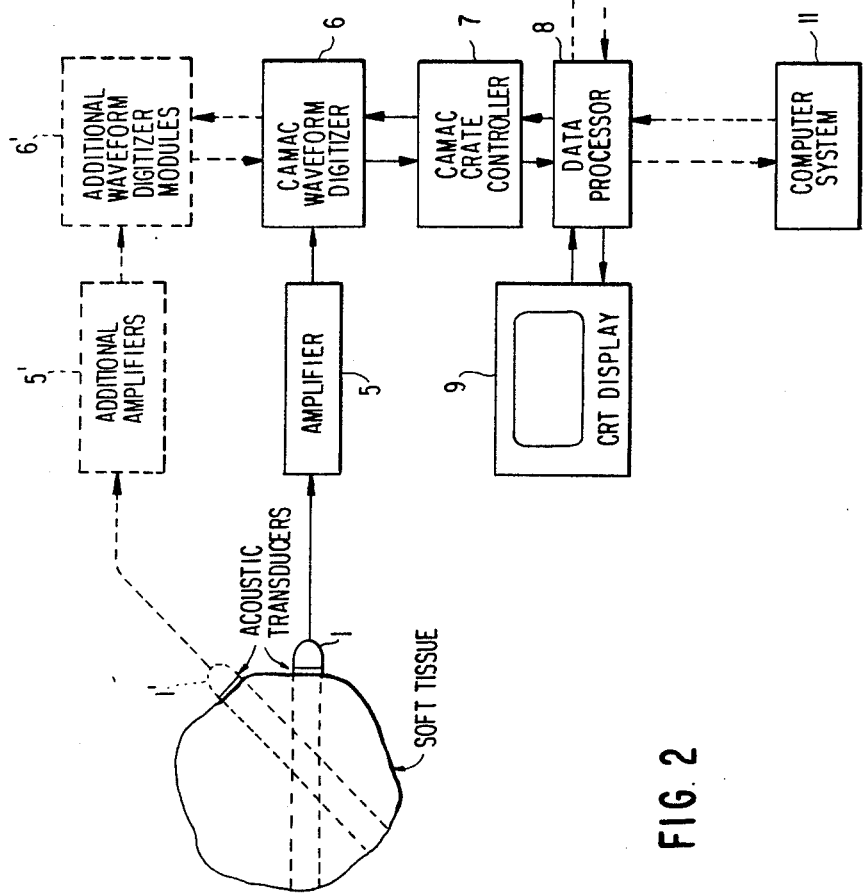
FIG. 2 is a block diagram of instrumentation for thermoacoustic imaging according to the invention.

A block diagram of the digital signal averaging hardware is shown in FIG. 2. It is based entirely upon commercially available plug-in CAMAC instrument modules and digital data processing hardware. The modular approach adopted permits adding additional channels for two-dimensional imaging as indicated by the dotted lines. The acoustic transducer 1 is connected to the input of amplifier 5, the output of which is supplied to a waveform digitizer 6. If two-dimensional imaging is desired, additional acoustic transducers 1', amplifiers 5' and digitizers 6' are employed as generally indicated in the FIGURE. The waveform digitizer (LeCroy Model 2264) will take up to 32K samples at a 4 MHz rate, storing an 8 bit word for each. At a 2 MHz sampling rate it can handle two inputs; at 1 MHz, four inputs; at 0.5 MHz, eight inputs. The digitizer module is designed to operate in a CAMAC crate, which provides all power and data connections. The crate must be equipped with a crate controller module 7 to interface the data to a minicomputer 8—in this case, a Digital Equipment Corp. LSI-11. The LSI-11 may be a stand-alone unit or may be in a CAMAC module. The minicomputer adds each sample word from the latest waveform to the corresponding sample word total for the previously digitized waveforms. When the desired number of pulses have been accumulated, the averages are displayed on a CRT terminal 9 in the form of a simulated waveform—this is the one-dimensional thermoacoustic image presented in an "A-scan" format. Of course, the computer could be programmed to provide other formats and numerical data. Also shown in FIG. 2 are a floppy disk storage system 10 to provide increased mass storage for the minicomputer and a computer system 11 which would interface with the minicomputer to increase the data processing capacity of the system. These are required for multipath signal acquisition for reconstruction of two dimensional images.

The thermoacoustic wave is generated by differences from point to point of the source function $$s(r) = \tau \beta(r) W(r) / C_p(r) \rho(r),$$

where the vector r specifies the position of the point, $\tau$ is the pulse length, $\beta(r)$ is the volume coefficient of expansion at r, W(r) is the power per unit volume deposited in the neighborhood of point r (pulse length assumed very small), $C_p(r)$ is the specific heat per unit mass at r, and $\rho(r)$ is the density at r. In mathematical terms, the thermoacoustic emission is generated by $\nabla S(r)$, so no emission would occur from the interior of a uniformly irradiated homogeneous medium. Thermoacoustic imaging would give information on the function S(r). Let us separately consider the two most likely forms of irradiation: (a) ionizing radiation and (b) non-ionizing electromagnetic radiation.

If ionizing radiation (X-rays, electrons, etc.) is employed to deposit heat pulses, the power deposited in soft tissue per unit volume will be approximately given by $$W(r) \approx a\rho(r)I(r),$$

where I(r) is the intensity of the ionizing radiation at point r. (If the L.E.T. of the radiation varies significantly with depth, this is assumed to be incorporated into the definition of I(r).) The source function becomes $$S(r) = a \mp \beta(r)I(r)/C_p(r). \text{ (Ionizing radiation)}$$

Now consider applications of measuring this function. To a first approximation, $\beta(r)/C_p(r)$ can be replaced by the average value of this ratio for soft tissue, probably not far from the value for water. Then, a measurement of S(r) over distances of many centimeters, ignoring local fluctuations, would measure I(r); this would be useful in verification of therapeutic irradiation to insure conformance with treatment planning. Now, considering the detailed fluctuations of S(r), these could be attributed to variations of $\beta(r)/C_p(r)$ from point to point due to changes of tissue composition and structure, assuming that I(r) is a smooth, slowly varying function of position. Hence, features of the tissue, organ, and tumor structures should be visible superimposed upon the broader profile of the illumination function I(r). The order of magnitude of the variations to be expected in $\beta/C_p$ can be obtained by comparing this ratio for various tissues. As shown in Table I, local variations of $\beta/C_p$ would be on the order of a factor of 2 assuming that $\beta$ is comparable for fat and olive oil, and for muscle and salt water. The application of this technique to therapeutic radiation treatments is emphasized because, although the expected S/N ratios are very promising with total doses ~100 rads, the S/N ratios become marginal for diagnostically acceptable doses $\lesssim 1$ rad.

TABLE I

Thermal properties of various soft tissues and related substances.

| Material | Temp. (°C.) | Vol. Thermal Exp. Coef, $\beta$ (°C$^{-1}$) | Specific Heat, $C_p$ cal-g$^{-1}$-°C.$^{-1}$ |
|---|---|---|---|
| Fat (human) | | | 0.55 |
| Fat (pig) | | | 0.62 |
| Muscle (human) | | | 0.91 |
| Muscle (pig) | | | 0.75 |
| Water | 37° | 3.64 × 10$^{-4}$ | 0.998 |
| Sea-water | 37° | 4.0 | 0.932 @ 17.5° C. |
| Olive oil | 37° | 7.44 | |

If non-ionizing radiation is employed for deposition of heat pulses, the energy deposited per unit volume per pulse may be a complicated function of the radiation intensity and the tissue properties. In the case of heating with an ultrasonic pulse having intensity proportional to $\exp(-2\alpha z)$, where z is the depth, $W(r) = 2\alpha(r)I(r)$, where I(r) is the intensity of the ultrasonic pulse at r. Then the thermoacoustic source function becomes $$S(r) = 2\tau\alpha(r)\beta(r)I(r)/C_p(r)\rho(r) \text{ (Ultrasonic heating)}$$

As in the case of ionizing radiation, S(r) on a scale of several centimeters would give the radiation intensity profile I(r), and smaller scale variations would be due to local fluctuations of $\alpha\beta/C_p\rho$ on the order of a factor of 2 with changes in soft tissue structure and composition.

In the case of heating with an RF radiation pulse with electric field E(r), the heat deposition depends upon the flow of current. If the major changes of tissue composition occur in layers, and if the electric field is roughly parallel to the layer interfaces, then the magnitude of E will be approximately the same in each layer, and the power deposition per unit volume will be $W(r) \approx \sigma(r)E^2(r)$ where $\sigma(r)$ is the electrical conductivity of the tissue at r. The thermoacoustic source function for this case is $$S(r) = \tau\beta(r)\sigma(r)E^2(r)/C_p(r)\rho(r) \text{ (Electric field parallel to tissue interfaces).}$$

Again, on a long distance scale, S(r) gives the profile of radiation intensity which is proportional to $E^2$. On a short distance scale one is observing variations of $\beta\sigma/C_p\rho$. Fatty tissue typically has a factor of 10 lower conductivity than tissues such as muscle, liver, spleen, and brain, so variations on the order of a factor of 10 would be expected in image features produced by electric fields parallel to major tissue interfaces.

If the electric field is normal to tissue interfaces, the current density J(r) would be approximately the same in each layer. Then the power deposited per unit volume would be $W(r) = J^2(r)/\sigma(r)$, and the thermoacoustic source function would be $$S(r) = \tau\beta(r)J^2(r)/\sigma(r)C_p(r)\tau(r) \text{ (Electric field perpendicular to tissue interfaces).}$$

On a long distance scale, S(r) would give the distribution of $J^2(r)$ which would be related to the radiation intensity. On a short distance scale the variations are proportional to $\beta/\sigma C_p\rho$, which again should vary by as much as a factor of 10 with tissue composition. Of course, the general case of RF heating would be a complicated combination of the foregoing equations for electric fields parallel and perpendicular to tissue interfaces.

It is evident that S(r) "images" would provide (a) useful information on the positioning of therapeutic radiation beams and (b) information on tissue structure and composition which may complement that obtained from standard techniques.

Widely available sources of therapeutic ionizing radiation are the Varian 4 and 18 MeV electron accelerators. Typical energy deposition densities from these accelerators are compared with comparable levels of RF and ultrasonic power deposition in Table II. The last column of Table II gives a S/N ratio figure of merit for the examples listed.

| Radiation source | Dose rate or Intensity | Pulse rate n | Thermoacoustic pulse length $\tau$ | Power/cm$^3$ W | S/N figure of merit n($\tau$W)$^2$ |
|---|---|---|---|---|---|
| 4 MeV electrons (Varian) | 356 rad/min | 320 Hz | 4 $\mu$sec | 46.3 mW/cm$^3$ | 0.11(rad)$^2$/s |
| 18 MeV electrons (Varian) | 333 rad/min | 300 Hz | 4 $\mu$sec | 46.3 mW/cm$^3$ | 0.10(rad)$^2$/s |
| 30 MHz RF | 20 W/cm$^2$ | 3,000 Hz | 1 $\mu$sec | 100 mW/cm$^3$ | 0.30(rad$^2$/s |

| Radiation source | Dose rate or Intensity | Pulse rate n | Thermoacoustic pulse length τ | Power/cm³ W | S/N figure of merit n(τW)² |
|---|---|---|---|---|---|
| 915 MHz RF | 2 W/cm² | 3,000 Hz | 1 μsec | 100 mW/cm³ | 0.30(rad)²/s |
| 1 MHz ultrasound | 1 W/cm² | 1,000 Hz | 4 μsec | 100 mW/cm³ | 1.6(rad)²/s |

The power deposition density W for the electron accelerators in Table II is determined by the manufacturer's design, and the pulse rate represents the maximum allowed by the design. The pulse rate for RF and ultrasonic heating is limited only by the necessity to allow all reverberations to die out between pulses; a somewhat longer time might be needed in the ultrasound case because the primary wave, itself, will produce reverberations. The power deposition density was arbitrarily set at 100 mW/cm³ for RF and ultrasonic radiation to indicate the intensity levels giving S/N figure of merit comparable to the case of ionizing radiation. This level of RF power deposition corresponds to the power, when continuously applied, which is reasonable for hyperthermic treatment, since 100 mW/cm³ would cause a temperature rise, neglecting perfusion and other losses, of 1.5° C./min. Of course, the temperature rise due to the pulsed radiation is reduced by the duty factor (3,000 Hz) $(10^{-6}s) = 3 \times 10^{-3}$ to an almost undetectable level.

In the case of ultrasonic heating, the intensity can be increased by a factor $\sim 10^3$ before lesions are noticeable which are probably due to cavitation. However, this advantage is offset by the disadvantages that the ultrasonic radiation does not simultaneously heat all points in the irradiated region and that the thermoacoustic emission is accompanied by scattered direct radiation which may be of greater amplitude. A technique for separation is to reverse the polarity of the transmitted wave each pulse: the scattered radiation from successive pulses should cancel and the termoacoustic radiation should coherently add. Other nonlinear acoustic mechanisms may also contribute to thermoacoustic radiation by ultrasound.

The pulse length of the electron accelerator pulses was chosen as long as possible without seriously degrading the resolution ($\sim 4$mm) discussed hereinbelow Sec. 2(c), since S/N ratio is proportional to $\tau^2$. With RF radiation, one is freer to shorten the pulse length to maximize resolution, since the loss in S/N ratio can be compensated by a higher pulse rate and higher power deposition density than for the electron accelerators. The ultrasonic pulse length cannot be arbitrarily shortened, since one must have at least one cycle, and higher frequencies are seriously attentuated.

Using Eq. (33) in the "Theory of Thermoacoustic Signals and S/N ratios" hereinbelow for the S/N ratio for detection of a thermoacoustic signal by a directional detector and the S/N figure of merit given in Table II, we obtain for the S/N ratio of data collected for time t:

$$\frac{S}{N} = \frac{\pi^{\frac{1}{2}} A c^2}{4kT\rho z^2}\left[\frac{\beta}{C_p}\right]_o^2 [n(\tau W)^2]\, \eta^3 t,$$

$$= 1.3 n_{Hz}(\tau W)^2_{erg}\, \eta^3_{cm}\, t_{sec},$$

$$= (1.3 \times 10^4)\, [n(\tau W)^2]_{(rad)2/s} \cdot \eta^3_{cm}\, t_{sec},$$

where we have assumed for these equations that $A = \pi(1.25\ \text{cm})^2$, $c = 1.5 \times 10^5\ cm/s$, $k = 1.38 \times 10^{-16}$ erg/° K., T = 310° K., $\rho = 1g/cm^3$, z = 10 cm, $\beta = 4 \times 10^{-4}$ C.$^{-1}$, $C_p = 3.8 \times 10^7 erg/g-°$ C., and $\eta$ is the size of the three-dimensional Gaussian source distribution $\exp(-r^2/2\eta^2)$. The S/N ratio of Eq. (33) should be reduced by a factor from 6 to 12 to allow for inefficient coupling, amplifier noise, and attenuation. If data is averaged for one minute, the actual S/N ratio would be $$(S/N)_{actual} \approx 10^5 [n(\tau W)^2_{(rad)2/s} \cdot \eta^3_{cm}$$

Using the figure of merit $\approx 0.3$ listed in Table II for RF radiation and changing the units of $\eta$ to millimeters, $$(S/N)_{actual} \approx 30 \eta^3_{mm}.$$

This last equation indicates that resolution $\eta \approx 1$ mm should be possible for RF and ultrasound induced thermoacoustic imaging.

THEORY OF THERMOACOUSTIC SIGNALS AND S/N RATIOS

Thermoacoustic waves are generated by a wide range of phenomena which suddenly dump heat into a finite region, and they have been "accidentally" observed in the case of chemical explosions, lightning, and even intense pulses of microwave radiation. However, the practical application of this effect for medical imaging depends upon observing very weak thermoacoustic waves which one would not expect to find by accident. The signals must be lifted out of the thermal noise background by high-speed digital signal averaging techniques which have only become practical in recent years. This cannot be expected to happen by chance, but rather by experimental work guided by a theoretical analysis of the results to be expected. This analysis will show that for medically reasonable doses one can expect to achieve good S/N ratios.

1. Estimation of the Thermoacoustic Signal (a) The basic equations:

Let us write down the first order, linearized acoustic equations for irrotational motion. These are:

Continuity $$\frac{\gamma}{c_0^2}\frac{\partial p}{\partial t} - \beta\rho\frac{\partial \theta}{\partial t} + \rho\nabla \cdot u = 0 \qquad (1)$$

Force $$\rho(\delta u/\delta t) = \rho F - \nabla p + (\eta' + 2\eta)\nabla(\nabla \cdot u) \qquad (2)$$

Energy $$\rho C_v(\delta\theta/\delta t) + (\rho C_v/\beta)(\gamma - 1)\nabla \cdot u + \rho C_v q\theta - \kappa\nabla^2\theta = W \qquad (3)$$

In equation (1) $\gamma$ is the ratio of specific heat $C_p/C_v$; $c_o$, the adiabatic speed of sound; $\rho$, the material density; $\beta$, the volume coefficient of thermal expansion; p, the pressure; $\theta$, the first order change in temperature, and u the vector particle velocity.

In equation (2), F is the external force per unit mass and the term $(\eta'+2\eta)\nabla(\nabla.u)$ is the viscous force per unit volume.

In equation (3), the term $\eta C_v q\theta$ arises due to radiation (q is the radiation coefficient), $\kappa$ is the heat conductivity, and W is the external heat input per second per unit volume.

Let us rewrite these equations using the following further assumptions: the heat radiation term is insignificant and can be dropped, there are no external forces, and the viscous force term is negligible. We then have instead of equations (2) and (3)

$$\rho(\delta u/\delta t) = -\nabla p \quad (2')$$

$$\rho C_v(\delta\theta/\delta t)+(\rho C_v/\beta)(\gamma-1)\nabla.u-\kappa\nabla^2\theta = W \quad (3')$$

Let us define $\Phi$, the thermoacoustic displacement potential, by the equation $$\xi = -\nabla\Phi \quad (4)$$

where $\xi$ is the vector position of the material particle. Then $$u = -\nabla\dot{\Phi} \quad (5)$$

and from equation (2')

$$p = \rho\dot{\Phi} \quad (6)$$

Substituting in equation (1) we have $$-\rho\nabla^2\Phi + (\gamma/C_0^2)\rho\ddot{\Phi} = \beta\rho\dot{\theta}$$

which upon integration yields $$\nabla^2\Phi - (\gamma/C_0^2)\ddot{\Phi} = -\beta\theta \quad (7)$$

Now, if $\rho\nabla.u$ is eliminated between equations (1) and (3') we have $$\rho C_p(\delta\theta/\delta t)-(C_p/\beta c_0^2)(\gamma-1)(\delta p/\delta t)-\kappa\nabla^2\theta = W$$

In the adiabatic approximation we may neglect the diffusion term so that this equation becomes $$\rho C_p(\delta\theta/\delta t)-C_p/\beta c_0^2)(\gamma-1)(\delta p/\delta t) = W$$

and, on introducing the time derivative of p from equation (6), and rearranging $$\beta\dot{\theta}-[(\gamma-1)/c_0]\ddot{\Phi} = \beta W/\rho C_p \quad (8)$$

Taking the first integral gives $$\beta\theta = (\beta/\rho C_p)\int W\,dt + [(\gamma-1)/c_0^2]\dot{\Phi}$$

Substituting in equation (7) we have $$\nabla^2\Phi - (\gamma/c_0^2)\ddot{\Phi} = -(\beta/\rho C_p)\int W\,dt - [(\gamma-1)/c_0^2]\ddot{\Phi}$$

or $$\nabla^2\Phi - (1/c_0^2)\ddot{\Phi} = -(\beta/\rho C_p)\int W\,dt \quad (9)$$

Assuming $W=W(r,t)$ is zero except during a short duration $\tau$ during which $W(r,t)=W(r)$ we have $$\nabla^2\Phi - (1/c_0^2)\ddot{\Phi} = -\tau\beta(r)W(r)/\rho C_p$$

or $$\Box^2\Phi = -S(r) \quad (10)$$

where $$\Box^2 = \nabla^2 - (1/c_0^2)(\delta^2/\delta t^2)$$

and $$S(r) = \tau\beta(r)W(r)/\rho C_p \quad (11)$$

Figure 3:
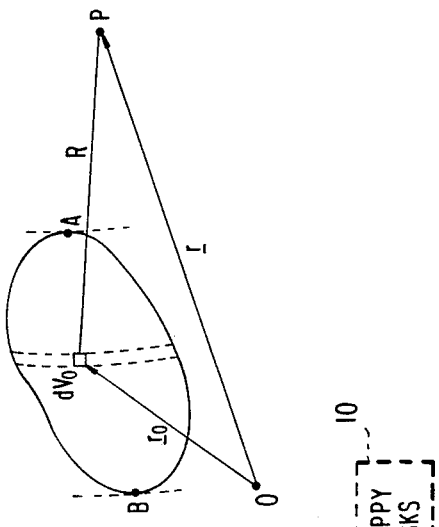
FIG. 3 illustrates the coordinate system used in developing the theoretical equations for thermoacoustic imaging.

(b) The general solution for the displacement potential:

The solution to equation (10) is given by Morse and Feshbach, *Methods of Theoretical Physics*, Pt. 1, McGraw-Hill (1953), p. 834:

$$\Phi(r,t) = (1/4\pi)\int dV_0 S(r_0)/R \quad R < ct \quad (12)$$

where $R=|r-r_0|=$distance from volume element $dV_0$ at $r_0$ to the point of observation at r, as shown in FIG. 3. The thermoacoustic source function S(r) corresponds mathematically to a distribution of electric charge; just as in the electrical case, the potential at point r is the sum of the retarded potentials from all fictitious charges $S(r_0)$. Since the fictitious charge was everywhere zero for $t<0$, at later time t only those regions within a sphere of radius $R=ct$ around the point P at r will contribute to the potential at that instant. As time progresses, the radius of the sphere grows with the speed of sound, c. When the radius $R=ct$ becomes large enough to enclose the entire region where $S(r)\neq 0$, the displacement potential $\Phi$ has reached its final value $\Phi\infty$ given by the equation for quasistatic equilibrium, $$\nabla^2\Phi_\infty = -S(r). \quad (13)$$

Figure 4A:
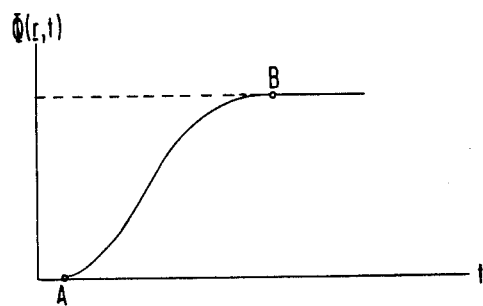
FIGS. 4a to 4c are graphs of dispacement potential, velocity potential, and pressure signal, respectively.

Since S(r) is always positive, $\Phi(r,t)$ must monotonically increase from zero to $\Phi\infty$, as shown in FIG. 4a. Note that the exact shape of the rise of $\Phi$ is determined by the rate at which the sphere of radius $R=ct$ encloses additional fictitious charge S(r). In the above discussion we have assumed that the heat pulse is deposited at $t=0$ everywhere, which is a good approximation for ionizing radiation and for electromagnetic radiation whose speed is much greater than the speed of sound; for heat deposition by ultrasonic radiation the specification of the integration volume in equation (12) versus time would be appropriately modified.

(c) Attenuation-independent properties of $\Phi\infty$:

Equations (7), (10), and (12) assume no attenuation of the acoustic waves in the medium, but equation (13) for $\Phi\infty$ is always valid for any type of attenuation, provided only that the attenuation vanishes as frequency approaches zero. Attenuation may slow down the rate of rise of $\Phi$ to its final value, but will not affect $\Phi\infty$. It is clear from equation (6) that $\Phi\infty$ can be obtained by a double time integration of the measured pressure p(t), which is also numerically equal to the first moment of p(t), and to the limit when $R\to\infty$ in equation (12):

$$\Phi_\infty(r) = \frac{1}{\rho}\int_0^\infty dt \int_0^t p(r,t')dt', \quad (14a)$$

$$= -\frac{1}{\rho}\int_0^\infty tp(r,t)dt, \quad (14b)$$

$$= \frac{1}{4\pi} \int dV_o \cdot \frac{S(r_o)}{R}, \quad (14c)$$

Equations (14a,b,c) are all exact, even in the presence of high frequency attenuation. Suppose the source function $S(r_o)$ has an isolated peak at $r_l$ having a size or spread small compared to the observation distance $R_l = |r-r_l|$. Then it is a reasonable approximation to take R outside the integral in equation (14c):

$$\Phi_\infty(r) \equiv \frac{1}{4\pi R_1} \int_{\substack{\text{Small}\\\text{Region}}} dV_o \cdot S(r_o) \quad (15a)$$

$$\equiv \frac{1}{4\pi R_1} \frac{\beta(r_1) E_o(r_1)}{C_p(r_1)\rho}, \quad (15b)$$

where $$E_o(r_1) = \tau \int_{\substack{\text{Small}\\\text{Region}}} dV_o \cdot W(r_o). \quad (16)$$

$E_o$ is the total heat energy deposited in the $S(r)$ peak. If there is such a peak in $S(r)$, the following paragraphs will show that it can be seen in the first time integral $I(t)$ of the pressure signal, and the location $t_1$ in time of this peak will directly give the observation distance $R_1 = ct_1$.

The relation using equations (14b) and (15b) was explicitly verified by the inventor and collaborators for energy deposition by 200 MeV protons in water (22). For clarity, equations (15a,b) were derived for a small region, allowing R to be taken outside the integral; since R can be obtained from the time delay in the pressure signal, it is not necessary to assume that the peak of $S(r)$ lies in a small region. If the peak in $S(r)$ is due to a radiation beam profile, then equations (14a or b) and (15b), when combined provide a means for an accurate measurement of the product $(\beta/C_p)(E_o)$. In some situations where an average value for $\beta/C_p$ is known, this relation may be useful for radiation dosimetry; in other cases where a known total energy was deposited in a finite volume, this will permit a determination of the average, $<\beta/C_p>$, for that volume.

(d) One-dimensional source profiles and the first time integral of the pressure:

Referring again to FIG. 3, if the observation point P is assumed far away from the heated region of interest in comparison with the size of the region, then the various concentric spherical surfaces shown by dashed lines approach planes, and the integral in equation (12) becomes a one-dimensional integral along the line of observation. Let the line from the center of the region of interest to the observation point define the z-axis. Then equation (12) becomes $$\Phi(z,t) = \frac{1}{4\pi} \int_{|z-z_o|<ct} \frac{dz_o}{|z-z_o|} \int dx_o dy_o S(x_o,y_o,z_o), \quad (17a)$$

$$= \frac{1}{4\pi} \int_{|z-z_o|<ct} \frac{dz_o}{|z-z_o|} \cdot s(z_o), \text{ where} \quad (17b)$$

$$s(z) \equiv \int dx\, dy\, S(x,y,z). \quad (18)$$

$s(z)$ is the one-dimensional projection of the thermoacoustic source function $S(r)$ on the line of observation. The extent of the integration over x and y in equation (18) is determined by the finite size of the region in which $S(r)$ differs from zero or a constant value; otherwise the approximation made in equation (17a) would not make sense.

Let us now use equation (17b) to calculate the time derivative of $\Phi(z,t)$, noting that the only time dependence on the right hand side is in the limit of integration:

$$\frac{\partial \Phi(z,t)}{\partial t} = \frac{s(z-ct)}{4\pi t}. \quad (19)$$

Figure 4B:
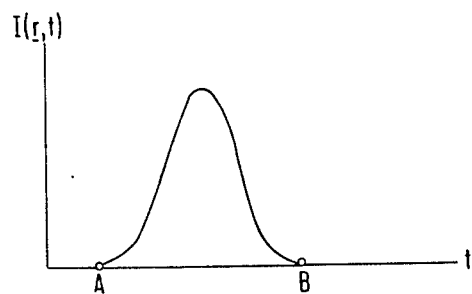

Equation (19) does not diverge at t=0 provided that the pressure observation point is outside the heated region, as it must be to justify the approximation made in equation (17a). Integrating equation (6) once with respect to time and combining with equation (19), we have $$s(z-ct) = \frac{4\pi t}{\rho} \int p(z,t')dt', \quad (20a)$$

$$= (4\pi t/\rho)I(z,t), \quad (20b)$$

where $I(z,t)$ is the first time integral of the pressure defined by equations (20a,b) and illustrated in FIG. 4b. So $I(z,t)$ which can be measured is directly related to the one-dimensional thermoacoustic source function $s(z)$. If the size of the source region is not small relative to the distance to the pressure detector or relative to the region of uniform response of a directional detector, then one should return to equation (12) to calculate $<\Phi>$, the displacement potential averaged over the sensitive area of the transducer, and use $<\Phi>$ in place of $\Phi$ in equation (6) to relate the apparent pressure to the thermoacoustic source function.

(e) The pressure signal:

If equation (20a) is differentiated with respect to time, we obtain $$p(z,t) = -\frac{\rho c}{4\pi t}\left\{\left[\frac{ds(z)}{dz}\right]_{z-ct} + \frac{s(z-ct)}{ct}\right\} \quad (21)$$

Figure 4C:
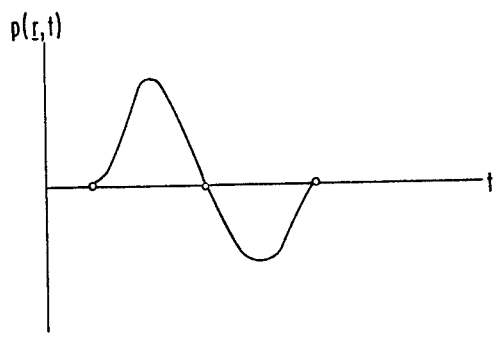

The second term in equation (21) may be neglected because of the assumption made in equation (17a) that the observation distance is large compared to the distance scale in which appreciable changes in $s(z)$ occur. Equation (21) confirms that the pressure signal is generated by the gradient of the thermoacoustic source function; the pressure is illustrated in FIG. 4c.

2. Estimation of the S/N Ratio (a) S/N ratio for a matched filter:

According to the statistical theory of signal processing in the presence of white noise the best possible signal-to-noise ratio of a transient signal is obtained from the output of a matched filter. For this ideal case the S/N ratio is given by $$\frac{S}{N} = \frac{2E}{N_o} = \left[2\int_0^\infty [p(t)]^2 dt\right]\left[\frac{d<v^2>}{df}\right]^{-1} \quad (22)$$

where the E in the numerator is proportional to the total energy in the transient pressure pulse and the denominator $N_o$ is proportional to the r.m.s. noise power per Hertz. It is clear that the evaluation of equation (22) is independent of any specific design parameters of the detector such as bandwidth or integration time constant. The assumption of white noise implies that $N_o$ is constant. If the pressure signal is not in a white noise background, we must prescribe a linear filter for the signal and noise such that the filtered noise is "whitened" before applying equation (22).

Figure 5:
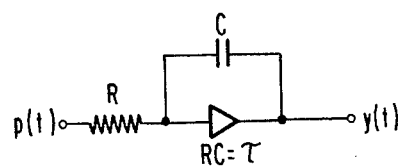
FIG. 5 is a schematic diagram of a filter to make "white" noise.

(b) Signal filtering and S/N for a point pressure detector:

In a region whose dimensions are large compared to the wavelengths λ of interest the thermal noise power measured by a detector whose dimensions are small compared to λ is proportional to $f^2$ and is given by $$\frac{d\langle p^2 \rangle}{df} = \frac{4\pi kT\rho}{c} f^2, \tag{23}$$

where k is the Boltzmann constant and T is the absolute temperature. If the pressure sensor responds uniformly as a function of frequency, then an electronic integrator is appropriate for whitening the noise given by equation (23). FIG. 5 shows the basic integrator circuit with time constant $\tau$. Ignoring gain factors which drop out in the S/N ratio, the integrator output y(t) for input p(t) is $$\frac{d(y^2)}{df} = \frac{1}{4\pi^2 f^2 \tau^2} \frac{d(p^2)}{df}. \tag{24}$$

where I(t) is defined by the time integral in equation (24). The noise output is $$y(t) = \frac{1}{\tau} \int_o^t p(t')dt' = \frac{I(t)}{\tau}, \tag{25}$$

Inserting equations (23-25) into equation (22), we obtain $$\frac{S}{N} = \frac{2\pi c}{kT\rho} \int_o^\infty I^2(t)dt. \tag{26}$$

In order to evaluate the integral in equation (26), the one-dimensional source function s(z) must be found from equation (18). The integration in equation (18) must converge because of the finite extent of the thermoacoustic source distribution S(r). Let us assume that S is given by a three-dimensional Gaussian with r.m.s. radius $\sqrt{3}\eta$:

$$S(r) = S_o \exp[-r^2/2\eta], \tag{27a}$$

$$s(z) = 2\pi \eta^2 S_o \exp[-z^2/2\eta^2], \tag{27b}$$

where equation (18) has been used to obtain equation (27b). Employing equation (20b) we find $$I(z,t) \approx \frac{\rho c \eta^2 S_o}{2z} \exp[-(z-ct)^2/2\eta^2], \tag{28}$$

where we have substituted $t \approx z/c$ in the denominator because we are assuming that $\eta << z$. Substituting I(z,t) from equation (28) into equation (26) and integrating, we obtain $$\frac{S}{N} = \frac{\pi^{3/2} c^2 \tau^2}{2kT\rho z^2} \left[ \frac{\beta W}{C_p} \right]_o^2 \eta^5, \tag{29}$$

where $[\beta W/C_p]_o$ is the peak value at z=0. (If the Gaussian peak is on top of an average background level $\langle \beta W/C_p \rangle$, then $[\beta W/C_p]_o = [\beta W/C_p]_{total}$ at $z=0$ $- \langle \beta W/C_p \rangle$).

In order to obtain an idea of the magnitude for S/N for conditions which may be achieved with a therapeutic electron beam while delivering a total dose of 100 rads, suppose $[\beta W/C_p]_o \approx \langle \beta W/C_p \rangle$ i.e., the maximum total value of S(r) is twice its background level. Then, if $c=1.5\times 10^5$ cm/s, $k=1.38\times 10^{-16}$ erg/°K., T=310° K., $\uparrow =1$ g/cm$^3$, z=10 cm, $\beta=4\times 10^{-4}$°C.$^{-1}$, $c_p=3.8\times 10^7$ erg/g-°C., $\tau W=2$ erg/cm$^3$, and $\eta=0.4$ cm, $[S/N]_{1\ pulse}=0.067$, $[S/N]_{5000\ pulses}=333$.

Since we employ the usual engineering definition of S/N ratio as an energy ratio, $[S/N]_n$ for n pulses is $n[S/N]_{1\ pulse}$. This result shows that thermoacoustic emissions associated with therapeutic doses of ionizing radiation should be able to exhibit image features with resolution ~4 mm; note that the S/N ratio given by equation (29) depends upon $\eta^5$. On the other hand, thermoacoustic emissions at this level are not likely to be observed accidentally.

(c) S/N for a directional pressure detector:

If the area A of a pressure detector is much greater than $\lambda^2$, where λ is the order of magnitude of the wavelengths of interest, then the noise spectrum is white and given by $$\frac{d(p^2)}{df} = \frac{kT\rho c}{A}. \tag{30}$$

Since the noise is already white, we can set y(t)=p(z,t) in equation (22) to calculate S/N and p(z,t) can be found from equation (21):

$$\frac{S}{N} = \frac{2A}{kT\rho c} \int_o^\infty [p(z,t)]^2 dt \tag{31}$$

Let us calculate S/N for the same Gaussian thermoacoustic source function employed in the preceding section equations (27a,b) positioned on the axis of peak detector sensitivity. The pressure signal is $$p(z,t) = (\rho c^2 S_o/2z)(z-ct)\exp[-(z-ct)^2/2\eta^2]. \tag{32}$$

Substituting p(z,t) from equation (32) into equation (31) and integrating, we obtain $$\frac{S}{N} = \frac{\pi^{\frac{1}{2}} A c^2 \tau^2}{4kT\rho z^2} \left[ \frac{\beta W}{C_p} \right]_o^2 \eta^3. \tag{33}$$

Comparing with equation (29) for the point pressure detector, the only change is the substitution of the detector area A in equation (33) in place of $2\pi\eta^2$ in equation (29). Since the important wavelengths λ must be the same order of magnitude as η, the assumption of a directional pressure detector guarantees that $$A \gtrsim 2\pi\eta^2; \tag{34}$$

therefore a directional detector generally improves the S/N ratio for on-axis sources. For $\eta=0.4$ cm employed in the example in the previous section, $2\pi\eta^2=1.01$ cm$^2$.

For this value of $\eta$, a 2.5-cm-dia. transducer would improve the S/N ratio by a factor of 5 relative to a point pressure detector. Or, if the S/N is maintained the same as in the preceding section, $\eta$ can be reduced to $\eta = 0.23$ for the 2.5-cm-dia. directional detector.

(d) S/N reduction factor due to attenuation:

The effect of attenuation of the higher frequencies upon the S/N ratios estimated for point pressure detectors equation (29) and directional detectors equation (31) can be obtained by expressing the integral in the numerator of equation (22) as an integral over the Fourier transform, $y(\omega)$, of the signal $y(t)$:

$$E = \int_{0\infty}^{\infty} [y(t)]^2 dt, \quad (35a)$$

$$= \int_{-\infty}^{\infty} |\bar{y}(\omega)|^2 d\omega, \quad (35b)$$

where $$\bar{y}(\omega) = [1/(2\pi)^{\frac{1}{2}}] \int_{-\infty}^{\infty} p(t) \exp(-i\omega t) dt. \quad (36)$$

In tissue, the acoustic attenuation coefficient is observed to increase very nearly linearly with frequency $f = \omega/2\pi$, so the corresponding signal Fourier component will be given by $$\bar{y}_{atten} = \bar{y} \exp(-\alpha f z), \quad (37a)$$

$$= \bar{y} \exp(-\alpha z \omega/2\pi), \quad (37b)$$

where $z$ is the distance from source to pressure detector and the constant $\alpha \approx 0.01$ $\mu$sec/mm for typical soft tissues.

If equations (36) and (37b) are substituted into equation (35b), an integral is obtained for the signal energy E which can be evaluated in terms of the complementary error function, erfc(x). The result is most conveniently expressed as a correction factor $(S/N)_{atten}/(S/N)_{w/o\ atten}$. For the point detector, one finds $$(S/N)_{atten}/(S/N)_{w/o\ atten} = [exp(Z^2)][erfc(Z)] \text{ (Point detector)}, \quad (38)$$

where $$Z = (\alpha c z/\eta)/2\pi \quad (39)$$

$$erfc(x) = 2/(\pi)^{\frac{1}{2}} \int_x^{\infty} \exp(-u^2) du. \quad (40)$$

Figure 6:
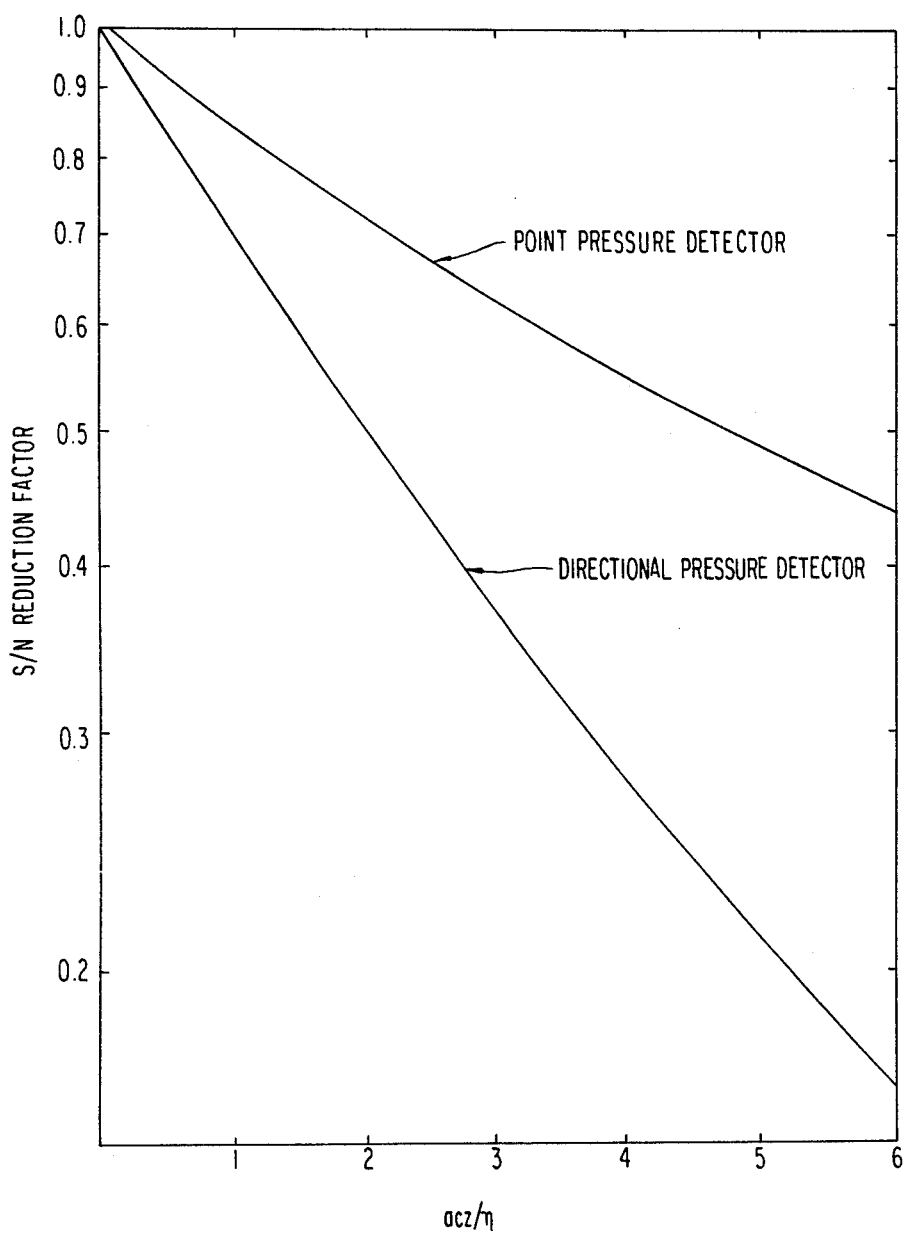
FIG. 6 is a graph of S/N reduction factor due to acoustic attenuation.

The S/N reduction factor given by equation (38) for a point detector is plotted in FIG. 6 (upper curve) as a function of $\alpha c z/\eta$. For the directional detector, $$(S/N)_{atten}/(S/N)_{w/o\ atten} = [1 + 2Z^2][exp(Z^2)][erfc(Z)] - 2Z/(\pi)^{\frac{1}{2}}. \quad (41)$$

where Z is defined in equation (39). This function is also plotted in FIG. 6 (lower curve). The directional detector signal is more rapidly attenuated because the signal wave form is bipolar, having falling intensity in the low frequency region, in contrast to the unipolar signal waveform of the of the integrated point detector signal which has a constant low frequency intensity.

The expression $\alpha c$ in equation (39) is a dimensionless constant characteristic of the medium; for tissue, $\alpha c \approx (0.01\ \mu\text{sec/mm}) (1.5\ \text{mm}/\mu\text{sec}) = 0.015$. If, for the point pressure detector, $\eta = 0.4$ cm and $z = 10$ cm as in Section 2(b), then $\alpha c z/\eta = 0.38$ and, from FIG. 6, the S/N reduction factor $\approx 0.93$. If reduction factors down to 0.5 were acceptable, signals could be received from depths to $z \approx 128$ cm.

If, as in Section 2(c) for the directional detector, $\eta = 0.23$ cm and $z = 10$ cm, then $\alpha c z/\eta = 0.65$ and, from FIG. 6, the S/N reduction factor $\approx 0.79$. If reduction factors down to 0.5 were acceptable, signals could be received from depths to $z \approx 31$ cm. Such figures indicate that soft tissue has sufficient acoustic transparency to permit thermoacoustic imaging.

(e) S/N reduction factor due to amplifier noise:

Pressure transducers can be divided into two classes: (1) parametric transducers which modulate the flow of externally-provided energy (the carbon microphone in the telephone is an example) and (2) energy-transforming transducers which transform mechanical energy into electrical energy (the piezoelectric transducer is an example). Although parametric amplification may introduce noise, it is theoretically possible for parametric amplification to be noise-free even with the system at finite temperature. In order to approximate the S/N ratios calculated for point pressure detectors in Section 2(b), a parametric transducer giving a large noise-free preamplication of the signal would be required. Although such schemes are under development for detection of gravity waves (29), the inventor is not aware of a practical noise-free parametric pressure transducer for the 1–1000 kHz frequency range. Energy-transforming transducers would be unsatisfactory for point detectors because the energy transformation efficiency is very low when transducer area $A << \lambda^2$.

In the case of directional pressure detectors, a piezoelectric transducer is equivalent to an antenna with a fixed electrical impedance, and the conversion efficiency between mechanical and electrical energy can be high ($\sim \frac{1}{2}$ is typical). The theoretical S/N ratio must be reduced by this conversion efficiency, by the noise introduced by an impedance-matching termination resistance at room temperature (factor $\sim \kappa$) and the noise figure of the amplifier (a low-noise amplifier with 1.5 db noise figure corresponds to a factor $\sim 0.7$). A typical overall S/N reduction factor due to inefficient coupling and amplifier noise might be $\sim 1/6$.

EXPERIMENT

Thermoacoustic waves were induced in soft tissue phantoms consisting of layers of muscle tissue phantom gel and vegetable oil by 0.4 microsec. duration electric current pulses. The acoustic signals were detected by a standard 1.6 MHz transducer designed for medical ultrasonic echo scanners after digital signal averaging of typically $10^3$ to $10^4$ waveforms. The observed signals had the amplitude and time-delay characteristics expected for thermoacoustic emission. Although the phantom interfaces represented the most favorable case which might be expected in normal soft tissue, the amplifier noise figure was rather high ($\sim 30$ db) and the transducer had a narrowband pass. The results support the feasibility of thermoacoustic imaging of soft-tissue by a transducer-amplifier-averaging system optimized for this application.

EXPERIMENTAL ARRANGEMENT

Figure 7:
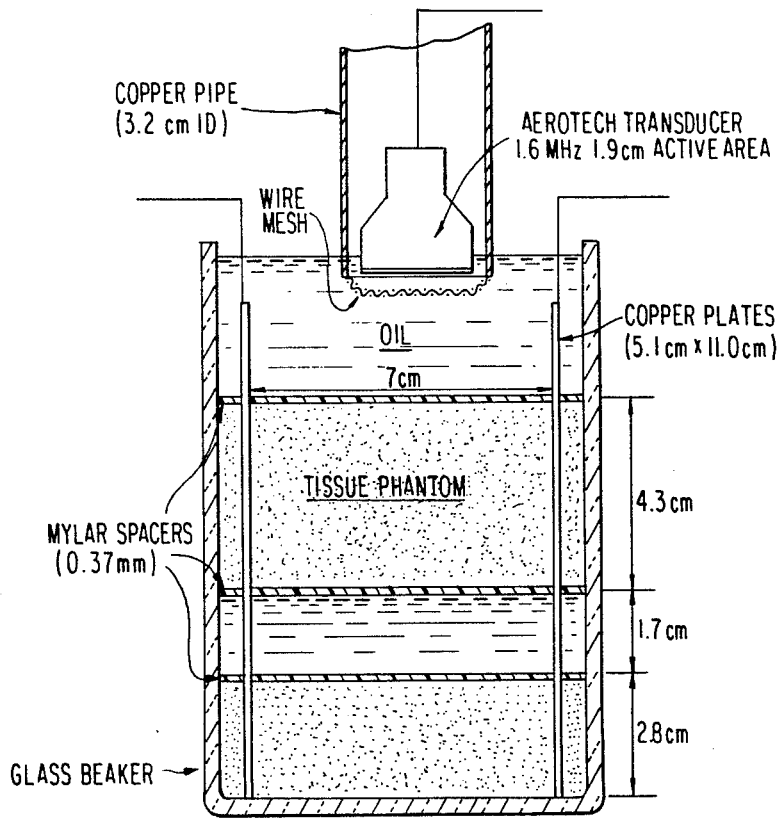
FIG. 7 illustrates the experimental arrangement of a four layer phantom tissue and an acoustic transducer.

The phantoms were constructed of layers of muscle phantom gel (Series B 14), which was formulated to simulate the electrical properties of muscle tissue at 2 MHz, and vegetable oil to simulate tissue with high lipid content. It had been earlier established that vegetable oil and animal lipids had very similar properties with respect to acoustic speed and the variation of speed with temperature. The electrodes were approximately 5.4 cm×11.4 cm spaced 7.0 cm apart. Layers of muscle phantom covered approximately 7 cm of the electrode length. The impedance in the 1 to 2 MHz region was close to 50 ohms and largely resistive. The construction of the 4-layer phantom within a 1000 mL beaker is shown in FIG. 7; the 2-layer phantom was similar to FIG. 7, but contained only a 7 cm thick layer of muscle phantom gel topped by a 5 cm thick layer of vegetable oil. With this method of construction, it was difficult to insure that each surface was level. However, the vertical beam arrangement with the phantom set on a Lab Jack for height adjustments turned out to be very convenient.

The arrangement of the transducer is also illustrated in FIG. 7. The Aerotech 1.6 MHz 19 mm dia. long focus (6–12 cm) unit is suspended by its connecting cable and positioned by foam pads within a 1¼″ i.d. copper pipe, the upper end of which was C-clamped to the chassis of the high-gain amplifier for grounding. The lower end of the copper pipe was covered by copper window screen which was held in place by a worm-screw type hose clamp.

Figure 8:
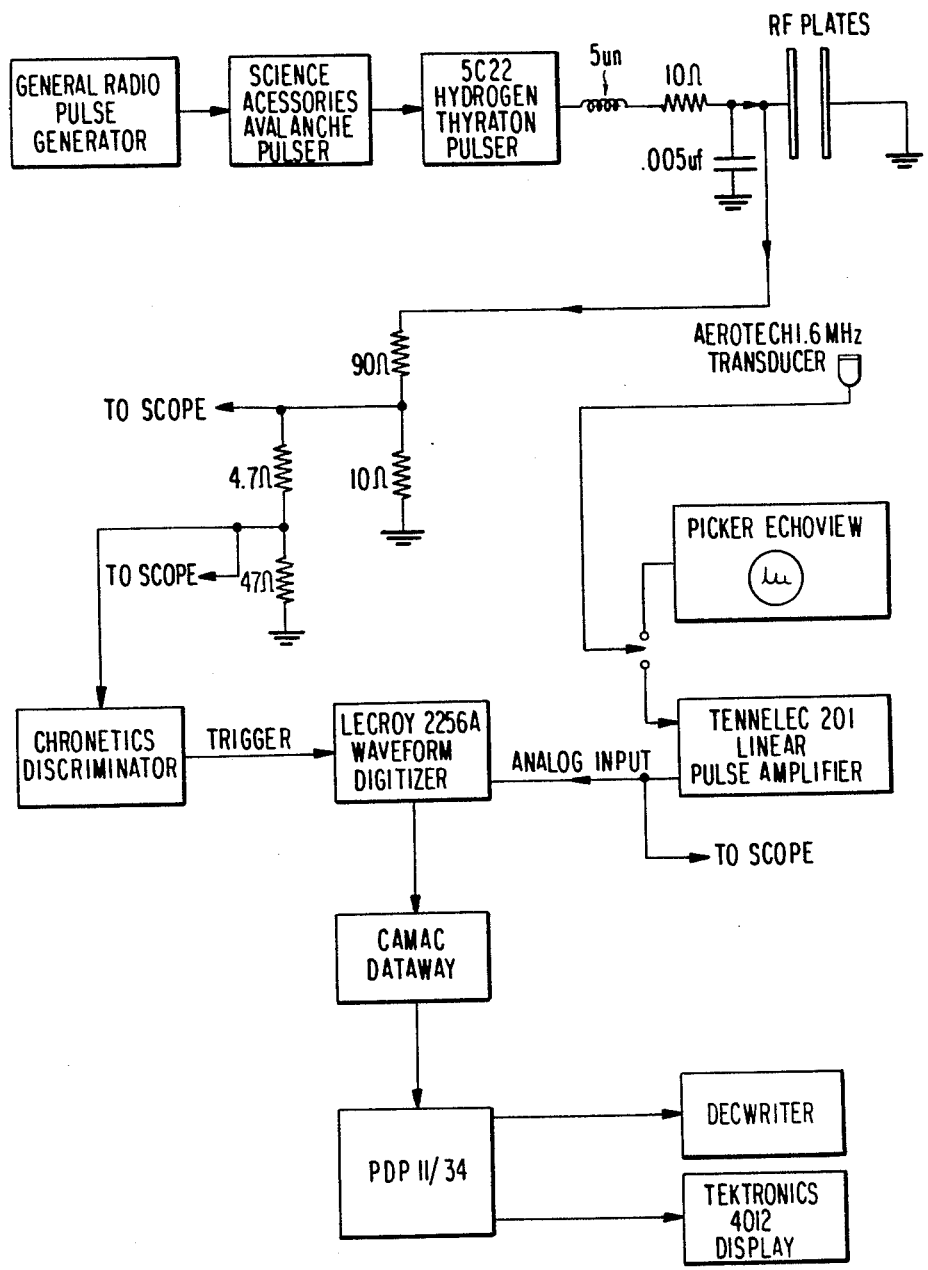
FIG. 8 is a block diagram of the experimental electronics used to demonstrate the imaging technique according to the invention.

The transducer cable could be connected either to the Picker Echoview employed in the A-mode, or to the input of a Tennelec Model 201 linear pulse amplifier (see FIG. 8). In the A-mode, one could ascertain that the oil was in contact with the transducer, and that the expected echoes from interfaces were not blocked or obscured by unseen air bubbles. Watching these echo returns as the phantom was tilted slightly, it became apparent that the lower oil-gel interface was tilted in the 4-layer phantom (the one illustrated in FIG. 7); this interface did not return a strong echo in the data-taking position of the phantom.

The Tennelec amplifier shown in FIG. 8 is designed primarily for use with solid state detectors employed in nuclear radiation detection applications. It is designed to have excellent gain stability and fast recovery from overloading transients. When set for flat frequency response (as done for this work), the bandwidth is approximately 3 MHz. The voltage gain from amplifier input to output when driving the 50 ohm load presented by the waveform digitizer was measured to be $G=317\pm32$, whereas $G=358$ was calculated from the panel settings ($G=512$) and the 93 ohm output impedance driving a 50 ohm load. The agreement between measured and expected gain is considered satisfactory, and the theoretical figure ($G=358$) was used for data analysis purposes. The r.m.s. noise of the amplifier, referred to the input, was determined from subsequent data analysis of digitized waveforms without signals to be 50 microvolts. Thus, the amplifier is rather noisy with a noise figure N.F.=30.3 db relative to noise-free operation with a 93 ohm input termination at 300° K., and even higher relative to a 50 ohm termination. For the runs with the 4-layer phantom, the input impedance was set at 93 ohms; with the 2-layer phantom this was reduced to 46 ohms by a paralleled 91 ohm resistance. The termination had the effect of reducing the ringing of the transducer element.

For the purposes of a preliminary feasibility investigation, r.f.-induced thermal pulses in a phantom appeared most practical. Electrical excitation is simple and can be varied over a wide amplitude range. The lowest frequency medical ultrasound transducer available at the time of the experiment was a 1.6 MHz unit. For efficient operation at this frequency, the thermal pulse must have a duration not greater than one-half cycle. This was most easily provided by a single pulse of current from the discharge of a 5,000 pF energy storage capacitor by a 5C22 hydrogen thyratron (see FIG. 8). A low-pass LC filter section was added inside the thyratron pulser to eliminate fast rise-time pulse components which tend to overload low-level amplifiers. The output resembled one-half cycle of a sine wave with a half-period (pulse width at the base line) of approximately 0.4 microseconds. Peak amplitudes in the range from 1.0 to 2.8 kilovolts were employed in this work, the adjustment being made by setting the voltage output of the d.c. power supply which recharges the energy storage capacitor.

In order to monitor the high voltage pulse on an oscilloscope, a 10:1 resistor voltage divider consisting of ten 10 ohm, 2 watt resistors was employed. The output of the divider was further reduced in a 100:1 resistor divider to provide a 1 to 3 volt pulse for triggering a Chronetics Model 151A discriminator set at a 0.1 volt triggering level (see FIG. 8). This discriminator, designed for use in high energy physics particle counting applications, provides a stable time reference, $t=0$, for the initiation of the waveform digitization process.

The amplified transducer waveform was digitized at 0.1 microsec. intervals for 102.4 microseconds following each high voltage heating pulse. The digitization was performed by a LeCroy Model 2256A 8-bit 20 MHz CAMAC instrumentation module. This module is designed for operation by plugging into a CAMAC "crate." CAMAC is a system of mechanical, electrical, and software standards, widely used in high energy physics experimentation and slowly gaining acceptance in other applications, which provides all the power and data connections necessary to operate the modules and transfer data between the module and a host computer.

The host computer in this work was a Digital Equipment PDP 11/34 system ooperating under RSX1 M connected to a Jorway CAMAC controller and crate. Printed data was provided by a DECwriter and graphical display by a Tektronix 4012 terminal. The system permitted the experimenters to write a program in FORTRAN which controlled the direct memory transfer of digitizer data via the CAMAC system, carried out the signal averaging and other numerical tasks, and reconstructed the averaged data as a waveform on the Tektronix 4012. All numerical averages from each data run were printed, and the 4012 display was photographed with a Polaroid camera.

If $V(i,j)$ is the voltage of the i-th sample (i runs from 1 to 1024) of the j-th waveform (j runs from 1 to N, where a typical value of N is 10,000), then the signal-averaged output $<V(i,j)>$ was computed as $$<V(i,j)> = (1/N) \sum_{j=i}^{N} V(i,j).$$

If N waveforms are averaged, the signal-to-noise amplitude ratio is increased by a factor N. In all the runs taken for this report the signals could not be discerned in single waveforms. Since no effort was spent to maximize the rate at which waveforms could be generated and digitized, we were limited to approximately 10 waveforms per second both the by power supply recharging the energy storage capacitor and by the time to transfer each waveform into the computer and add it to the previous totals. The CAMAC system is capable of transferring one 24 bit word per microsecond, or one 1024 word waveform in approximately 1 millisecond.

RESULTS

Figure 9:
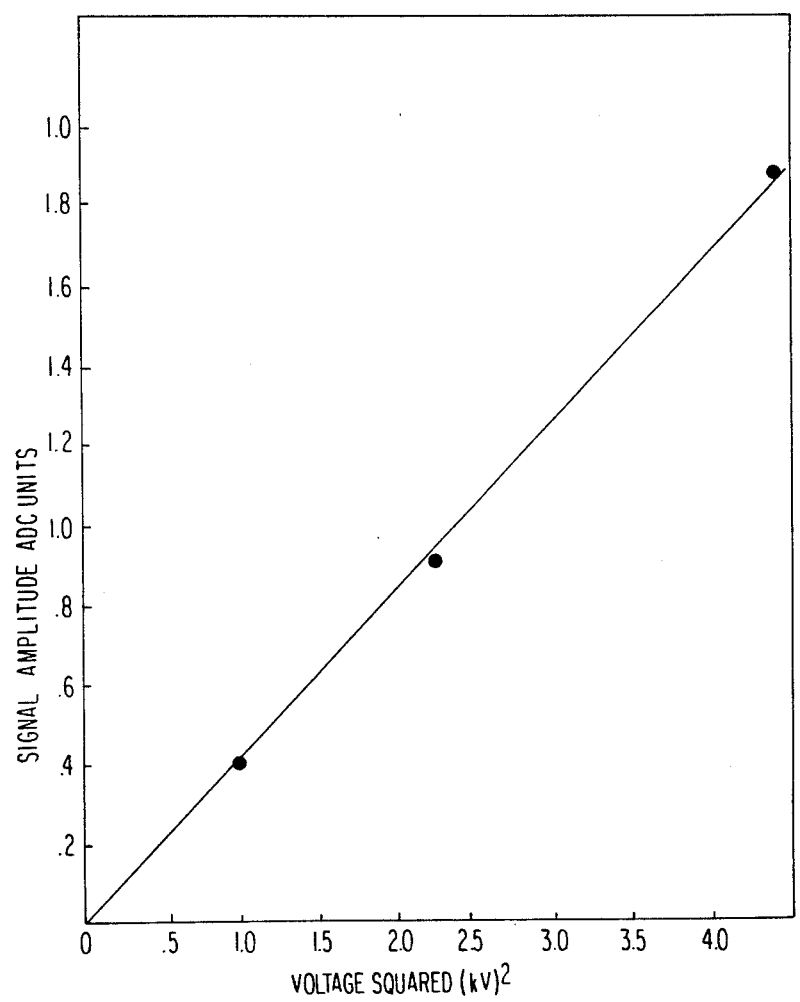
FIG. 9 is a graph of signal amplitude vs. peak heating voltage squared based on experimental results.

FIG. 9 shows the signal amplitude versus the square of the peak heating voltage. Thermoacoustic emission requires that these quantities by linearly related because the acoustic wave amplitude is proportional to the stress caused by thermal expansion. Thermal expansion, in turn, is proportional to the increment of heat energy, which is proportional to heating voltage squared if the resistance and pulse length remain constant. Dielectric stress (electrostriction) is proportional to electric field squared, which would also exhibit a $V^2$ dependence of acoustic amplitude. We did not carry out tests to evaluate the relative importance of these two mechanisms, such as insulating the electrodes to greatly reduce the flow of heating current. However, if dielectric stress turns out to be important in certain field configurations, it would augment the acoustic signal. Whereas the current flow tends to thermally expand the electrically conductive tissue, the electric field across low conductivity tissue tends to contract such regions.

FIG. 10 shows the signal delay versus distance from the transducer to the interface between media; the relationship agrees exactly with that expected for an acoustic wave generated at the interface at $t=0$ which propagates directly to the transducer.

FIG. 11 shows the signal amplitude as a function of distance from the transducer to the interface. It may seem surprising that the amplitude decreases at short distance. We believe this is attributable to moving out of the focal zone of the transducer, combined with a strongly peaked response of the system to high frequency signal components. If the interface were not precisely normal to the transducer beam axis, the signal would become broader in time as one moves out of the focal zone. In an optimized system it would be important to maintain response down to lower frequencies.

The averaged waveforms employed for the data of FIGS. 9, 10, and 11 are shown in FIG. 12. It might be asked why there is no signal visible from the bottom interface with the beaker. This surface was not flat and gave a broad echo on the Picker; we believe improved low-frequency response is required to exhibit a signal for such a case.

The averaged waveforms obtained from the 4-layer phantom are shown in FIG. 13, along with the display observed in the Picker Echoview under the same conditions. The lowest interface between the oil and gel, and the bottom interface to the beaker do not give strong echos. Tilting the phantom indicated that these surfaces were slightly inclined. This tilt, combined with a distance near the end of the focal zone, probably accounts for the small amplitudes of possible signals at the corresponding delays.

COMPARISON WITH THEORY

Although optimal matched filtering was not applied to separate the signal from the noise as assumed in the theory presented above, order-of-magnitude comparisons may be made. Equation (33) predicts the signal-to-noise ratio for a directional detector; the ratio of signal amplitude to noise amplitude is approximately the square root of the expression in equation (33):

$$\text{Sig. ampl./Noise ampl.} = c\beta\omega\tau(\pi A\eta^3 N)^{1/2}/2(kT\rho)^{1/2}C_p z,$$

where c is the speed of sound, $\beta$ is the thermal expansion coefficient, $\omega\tau$ is the energy deposited per unit volume in each pulse, A is the transducer area, $\eta$ is a distance characterizing the spatial resolution, N is the number of pulses averaged, k is the Boltzmann constant, T is the absolute temperature, $\rho$ is the density, $C_p$ is the specific heat per unit mass, and z is the distance from the signal source to the transducer.

Table III lists values for the above quantities appropriate for the 1 kilovolt data run plotted in FIG. 9 and shown in FIG. 12. The most uncertain parameter is $\eta$, the effective resolution. It was assumed that in a narrow band system its value is some fraction of a wavelength; we chose $\eta = \lambda/2$. The predicted signal-to-noise amplitude ratio is 270 for a noiseless termination and amplifier; the observed ratio was approximately 9. At 46 ohms input impedance the amplifier introduced a factor of 31 more r.m.s. noise over the thermal level, which accounts for the order of magnitude of the discrepancy between observed and calculated signal-to-noise rations.

TABLE III

List of parameters for calculating the signal-to-noise ratio. The numerical values correspond to the 1 kilovolt run plotted in FIG. 9 and whose averaged waveform is shown in FIG. 12.

| Parameter | Symbol | Value |
| --- | --- | --- |
| Speed of sound | c | $1.5 \times 10^5$ cm/s |
| Thermal expansion coefficient | $\beta$ | $4 \times 10^{-4}$/°C. |
| Heat energy density per pulse | $W\tau$ | 91 erg/cm$^3$ (= 0.91 rad) |
| Transducer area | A | 2.84 cm$^2$ |
| Resolution distance | $\eta$ | 0.047 cm (= $\lambda/2$) |
| Number of pulses averaged | N | 40,000 |
| Boltzmann constant | k | $1.38 \times 10^{-16}$ erg/°K. |
| Absolute temperature | T | 300° K. |
| Density | $\rho$ | 1 g/cm$^3$ |
| Specific heat | $C_p$ | $4.19 \times 10^7$ erg/°C.-g |
| Source-to-transducer distance | z | 5.4 cm |
| Signal amplitude / Noise amplitude | (calculated for noiseless termination and amplifier) | 270 |
| | (experimentally observed with noisy amplifier - see text) | 9 |

CONCLUSION

Using available instruments and a medical ultrasound transducer, short electrical pulses in a phantom have been observed to induce acoustic signals whose properties agree with the predictions of the theory of thermoacoustic emission. The observed signal-to-noise ratios, after signal averaging on the order of 10,000 pulses, agree in order of magnitude with theoretical estimates where account is taken of the rather noisy amplifier employed in the experiments. In a phantom with multiple interfaces, those interfaces which gave sharp conventional ultrasound echoes also produced observable thermoacoustic signals.

The experimental system had two serious deficiencies which can be remedied with further work: (1) The amplifier degraded the signal-to-noise amplitude ratio by a factor on the order of 30; it should be possible to improve this by a factor of 15. (2) The transducer response fell rapidly for frequencies below its resonant frequency; a transducer system with a response extending to lower frequencies and/or with a lower resonant frequency would be more suitable. Transducers which incorporate parametric amplification deserve study and development for this application since they offer the potential of negligible signal-to-noise degradation.

Finally, when ultrasonic echo signals are so large and relatively easy to obtain when compared to the efforts required to obtain clear thermoacoustic signals (and eventually images), the basic reason for these efforts merits repetition: Since thermoacoustic emission responds to different properties of the tissue than do echoes, thermoacoustic imaging offers a new dimension of non-invasive tissue measurement.

I claim:

1. A method of radiation-induced thermoacoustic imaging to non-invasively detect the composition and structure of a body, comprising the steps of
   inducing within a volume under investigation in said body a sudden thermal stress by a pulse of radiation which deposits energy causing a rapid, but very small, rise in temperature throughout said volume, and
   receiving the thermoacoustic signal emitted from within said volume as a result of the induced sudden thermal stress, thereby producing an image of inhomogenieties within said volume.

2. The method of claim 1 further comprising the step of signal-averaging the received signals produced by many successive pulses of radiation.

3. The method of claims 1 or 2 wherein the step of inducing a sudden thermal stress is performed with a pulse of ionizing radiation.

4. The method of claims 1 or 2 wherein the step of inducing a sudden thermal stress is performed with a pulse of non-ionizing radiation.

5. The method of claim 2 further comprising the step of displaying the signal-averaged signals to produce image features of the composition and structure of said body.

6. A method of non-invasive thermoacoustic imaging of soft-tissue regions in humans and animals, comprising the steps of
   coupling at least one acoustic transducer with the surface of a region to be investigated,
   inducing within said region sudden thermal stresses by a series of pulses of radiation which deposit energy causing rapid, but very small, rises in temperature throughout said region,
   receiving the thermoacoustic signals emitted from within said region as a result of the induced thermal stresses, and
   signal-averaging the received signals produced as a result of the induced sudden thermal stresses, thereby producing an image of inhomogenieties within said region.

7. The method of claim 6 comprising the step of displaying the signal-averaged signals to produce image features of the composition and structure of said region.

8. The method of claim 6 wherein the step of coupling is performed by coupling two or more acoustic transducers with the surface of said region to be investigated, each of said transducers being positioned about the periphery of said region and the receiving beam patterns of all of said transducers being on the same place.

9. The method of claim 6 wherein the step of inducing is performed so that the rise in temperature is between $10^{-8}°$ and $10^{-4}°$ C.

10. Apparatus for non-invasively detecting the composition and structure of a body by radiation-induced thermoacoustic imaging, comprising:
    means for inducing within a volume under investigation in said body a sudden thermal stress by a pulse of radiation which deposits energy causing a rapid, but very small, rise in temperature throughout said volume, and
    means for receiving the thermoacoustic signal emitted from within said volume as a result of the induced sudden thermal stress, thereby producing an image of inhomogenieties within said volume.

11. The apparatus of claim 10 wherein said means for inducing a sudden thermal stress includes a source of ionizing radiation.

12. The apparatus of claim 11 wherein the ionizing radiation is an electron beam.

13. The apparatus of claim 11 wherein the ionizing radiation is a beam of photons.

14. The apparatus of claim 13 wherein the beam of photons is an x-ray beam.

15. The apparatus of claim 11 wherein said ionizing radiation is a beam of neutrons.

16. The apparatus of claim 11 wherein said ionizing radiation is a beam of charged particles.

17. The apparatus of claim 10 wherein said means for inducing a sudden thermal stress includes a source of non-ionizing radiation.

18. The apparatus of claim 17 wherein said non-ionizing radiation is RF radiation.

19. The apparatus of claim 17 wherein said non-ionizing radiation is microwave radiation.

20. The apparatus of claim 17 wherein said non-ionizing radiation is ultrasonic radiation.

21. The apparatus of claim 10 further comprising means for signal-averaging the received signals produced by many successive pulses of radiation.

22. The apparatus of claim 21 wherein said means for signal-averaging comprises:
    digitizer means connected to said means for receiving and receiving an analog signal therefrom, said digitizer means sampling said analog signal at a high rate and providing at its output a digital word corresponding to each analog sample, and
    computer means connected to said digitizer means and receiving the digital words therefrom, said computer means computing an average of said digital words.

23. The apparatus of claim 21 further comprising display means for displaying the signal-averaged signals to produce image features of the composition and structure of the body.

24. Apparatus for non-invasively imaging soft-tissue regions in humans and animals by means of thermoacoustic imaging, comprising:
    at least one acoustic transducer coupled with the surface of a region to be investigated, means for inducing within said region sudden thermal stresses by a series of pulses of radiation which deposit energy causing rapid, but very small, rises in temperature throughout said region, means for receiving the thermoacoustic signals emitted from within said region as a result of the induced thermal stresses, and means for signal-averaging the received signals produced as a result of the induced sudden thermal stresses, thereby producing an image of inhomogeneities within said region.

25. The apparatus of claim 24 wherein said means for inducing a sudden thermal stress includes a source of ionizing radiation.

26. The apparatus of claim 24 wherein said means for inducing a sudden thermal stress includes a source of non-ionizing radiation.

27. The apparatus of claim 24 further comprising display means for displaying the signal-averaged-signals to produce image features of the composition and structure of said region.

* * * * *